United States Patent
Senelier et al.

(10) Patent No.: US 9,175,803 B2
(45) Date of Patent: Nov. 3, 2015

(54) ADJUSTABLE POSITION LOAD SUPPORTING ARM, LOAD SUSPENDING DEVICE

(71) Applicant: MAQUET SAS, Ardon (FR)

(72) Inventors: Gregory Senelier, La Marolle en Sologne (FR); Benoit Theodon, Orleans (FR)

(73) Assignee: MAQUET SAS, Ardon (FR)

( * ) Notice: Subject to any disclaimer, the term of this patent is extended or adjusted under 35 U.S.C. 154(b) by 105 days.

(21) Appl. No.: 13/859,365

(22) Filed: Apr. 9, 2013

(65) Prior Publication Data

US 2013/0264449 A1 Oct. 10, 2013

(30) Foreign Application Priority Data

Apr. 10, 2012 (FR) ...................................... 12 53259

(51) Int. Cl.
| | |
|---|---|
| *E04G 3/00* | (2006.01) |
| *F16M 13/02* | (2006.01) |
| *F16M 11/10* | (2006.01) |
| *F16M 11/20* | (2006.01) |
| *F16M 11/24* | (2006.01) |
| *A61B 19/00* | (2006.01) |

(52) U.S. Cl.
CPC .............. *F16M 13/022* (2013.01); *A61B 19/26* (2013.01); *F16M 11/10* (2013.01); *F16M 11/2014* (2013.01); *F16M 11/2092* (2013.01); *F16M 11/24* (2013.01); *A61B 2019/263* (2013.01); *A61B 2019/265* (2013.01); *A61B 2019/266* (2013.01); *F16M 2200/024* (2013.01); *F16M 2200/044* (2013.01)

(58) Field of Classification Search
CPC . F16M 13/022; F16M 11/10; F16M 11/2014; F16M 11/2092; F16M 11/24; F16M 2019/265; F16M 2200/924; F16N 2200/044; A61B 19/26; A61B 2019/263; A61B 2019/266
USPC .................... 248/276.1, 281.11, 284.1, 282.1
See application file for complete search history.

(56) References Cited

U.S. PATENT DOCUMENTS

| | | | | |
|---|---|---|---|---|
| 871,400 | A | * | 11/1907 Hall ......................... | 248/281.11 |
| 1,050,672 | A | * | 1/1913 MacIntosh ............... | 248/281.11 |

(Continued)

FOREIGN PATENT DOCUMENTS

| | | |
|---|---|---|
| DE | 1466999 A1 | 4/1969 |
| DE | 19501028 A1 | 7/1996 |
| FR | 2908497 A1 | 5/2008 |

OTHER PUBLICATIONS

French Search Report for FR 1253259, dated Jan. 22, 2013.

*Primary Examiner* — Amy Sterling
(74) *Attorney, Agent, or Firm* — Sughrue Mion, PLLC

(57) ABSTRACT

An adjustable-position load supporting arm (4) comprises a framework having the shape of a deformable parallelogram one free end (5) of which is able to support a load and a jack (12) able to deform the deformable parallelogram, the jack (12) being of the adjustable-pressure type so that the pressure inside the jack (12) is adjustable according to the weight of said load supported by the supporting arm (4). It comprises, at the free end (5), a connecting piece (6) able to support said load and has, in a first configuration, an axis of orientation (A) that is fixed with respect to said fixed link (9a) and, in a second configuration, an axis of orientation (B) that is variable with respect to said fixed link (9a) when said supporting arm (4) shifts position.

7 Claims, 6 Drawing Sheets

(56) References Cited

U.S. PATENT DOCUMENTS

| | | | |
|---|---|---|---|
| 3,160,379 A | | 12/1964 | Gardella |
| 6,012,693 A | * | 1/2000 | Voeller et al. ............ 248/280.11 |
| 7,546,994 B2 | * | 6/2009 | Altonji et al. .............. 248/276.1 |
| 2004/0084587 A1 | | 5/2004 | Oddsen |
| 2004/0188578 A1 | | 9/2004 | Turner |
| 2008/0111042 A1 | * | 5/2008 | Papendieck et al. .......... 248/325 |
| 2011/0315843 A1 | | 12/2011 | Hung |

* cited by examiner

ADJUSTABLE POSITION LOAD SUPPORTING ARM, LOAD SUSPENDING DEVICE

TECHNICAL FIELD

The invention relates to an adjustable-position load supporting arm comprising a framework having on the whole the shape of a deformable parallelogram and provided with at least a fixed link, a mobile link, a first and a second mobile connecting rod and a free end able to support a load.

The invention also relates to a load suspending device comprising such a supporting arm.

PRIOR ART

More particularly, the invention applies to a supporting arm for a suspending device intended to be used in a medical environment, in particular in an operating room.

A suspending device for an operating room comprises in a general way one or more supporting arms, which can be articulated and suspended to the ceiling of the operating room an which are intended to support a load such as for example an equipment such as a lighting device, a monitor, a camera, etc, or a medical device such as a transfusion or perfusion bottle, etc.

As it is known, the supporting arm comprises at least one tilting element having the shape of a deformable parallelogram, by means of which the supporting arm enables the user to modify in an easy and stable way the angular position of the arm in order to manually position the load for example at a desired height. The user can then put or remove a load once the supporting arm is blocked in position.

To this end, it is known to provide the above-described supporting arm with a mechanism comprising a pneumatic jack which can be provided with a mechanism for blocking the jack. For example, such a supporting arm is known from patent document FR 2 899 309. One drawback of such a supporting arm is that the jack is adapted to support a reduced range of weighting loads. Moreover, the jack of this supporting arm is fixed so as to, on the one hand, position the supporting arm into some desired position or other when the supporting arm supports a load and, on the other hand, to drive the supporting arm into a predetermined inoperative position when the supporting arm does not support any load. For putting a load at the free end of the tilting element, the user must position the supporting arm into this predetermined blocking position in which the mechanism for blocking the jack can block the supporting arm. The user must then move the supporting arm beyond the blocking position thereof in order to be able to unblock and position the supporting arm at the desired place. In some cases, this single predetermined blocking position can be difficult to be reached by the user and not adapted to receive a load.

An adjustable-position load supporting arm is also known from patent documents US-2004/188578, US-2011/315843, FR-2908497, US-2004/084587 and DE-19501028.

DISCLOSURE OF THE INVENTION

The purpose of the invention is to propose another adjustable-position load supporting arm which is able to support various loads and to be loaded in several positions.

For this purpose, the object of the invention is an adjustable-position load supporting arm comprising a framework having on the whole the shape of a deformable parallelogram and provided with at least a fixed link, a mobile link, a first and a second mobile connecting rod and a free end able to support a load, a jack comprising a body and a piston one of which is coupled with the fixed link and the other of which is coupled with at least one of the first and second connecting rods, said jack being able to actuate said first and second connecting rods with respect to said fixed link so as to deform said deformable parallelogram, said jack being of the adjustable-pressure type so that the pressure inside said jack can be adjusted according to the weight of said load supported by said supporting arm, wherein it comprises, at said free end, a connecting piece able to support said load and to be firmly connected to:

in a first configuration, said mobile link so as to have an axis of orientation that is fixed with respect to said fixed link and variable with respect to said first and second connecting rods when said supporting arm shifts position, in a second configuration, at least one of said first and second connecting rods so as to have an axis of orientation which is variable with respect to said fixed rod and fixed with respect to said first and second connecting rods when said supporting arm shifts position.

With such a load supporting arm, when putting a load onto the supporting arm, for example in order to replace a load with another load having a different weight, i.e. a heavier or lighter load, a user adjusts the interior pressure in the jack according to the weight of this other load. The supporting arm according to the invention is thus compatible with a large variety of equipments or devices. Moreover, the user can fix to the supporting arm a load whose axis will remain either parallel to the width of the parallelogram, i.e. the load is maintained vertical whatever the slope of the supporting arm, or to the length of the parallelogram, i.e. the axis of the load follows the slope of the jack of the supporting arm whatever the slope of the supporting arm.

Such a load supporting arm according to the invention can advantageously have the following features:

the supporting arm comprises a device for blocking the angular position of the first, second connecting rod with respect to the fixed link, the blocking device comprising a toothed rack and a latch one of which is firmly connected to the body of the jack and the other of which is firmly connected to the piston of the jack, the latch being arranged so as to be mobile along the toothed rack and able to cooperate with said toothed rack so as to block the angular position of the first, second connecting rod with respect to the fixed link in a plurality of blocking positions. Advantageously, the load change is thus easy and ergonomic for the user who can block the supporting arm in some desired position or other in order that the user can put a load onto the supporting arm or replace the load with another;

the latch comprises at least one cog intended to be inserted into a notch in the toothed rack in order to block the supporting arm in position. Inserting the cog into a notch in the toothed rack enables to block very efficiently the latch in the toothed rack and thus the supporting arm, for a wide range of weighting loads. As a comparison, friction blocking devices are not sufficient for retaining the supporting arm if the load is too heavy;

the supporting arm comprises a valve coupled with the jack and intended to connect said jack to a device for adjusting the pressure in the jack;

the supporting arm comprises at least one shell forming the second connecting rod jacketing the first connecting rod;

the first connecting rod has the shape of a Y whose basis is pivotally mounted on the fixed link, one branch of which has its free end pivotally mounted on the mobile link and the other branch of which has its free end connected to one end of the jack, the other end of the jack being able to pivot with respect to the fixed link.

The invention applies to a load suspending device comprising at least one articulated arm a first arm of which is arranged so as to be rotatable according to a rotational movement in a first plane and a supporting arm according to the invention connected to the first arm by means of a pivot joint arranged so as to rotate according to a rotational movement in a second plane distinct from the first plane.

BRIEF DESCRIPTION OF THE DRAWINGS

The present invention will be better understood and other advantages will clearly arise from the detailed description of an embodiment given as a nonrestrictive example and represented in the annexed drawings in which.

DESCRIPTION OF AN EMBODIMENT

Figure 1:
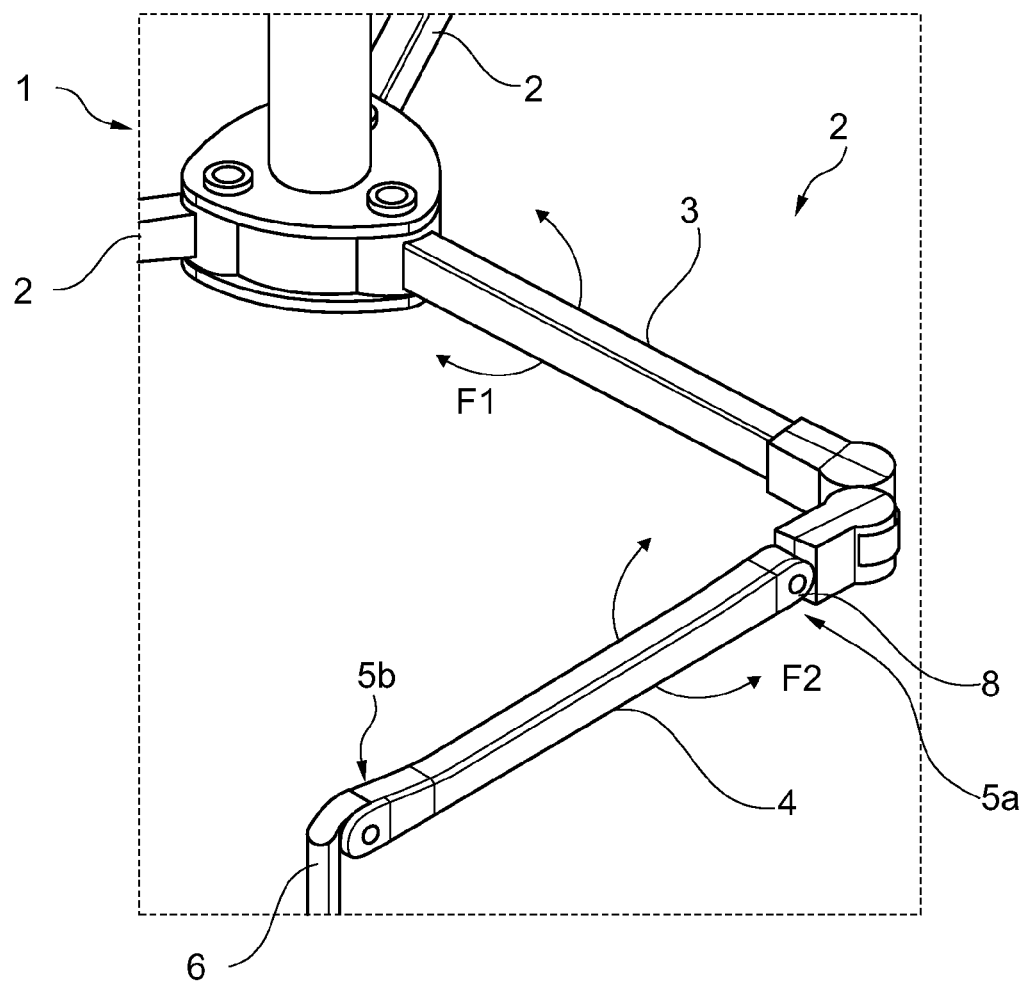
FIG. 1 is a perspective view of a load suspending device comprising a supporting arm according to the invention.

In FIG. 1, it is represented schematically a load suspending device 1 for a load (not represented) in an operating room, designed here to be suspended on the ceiling of the operating room, and comprising in the illustrated example three articulated arms 2 of which only one is shown as a whole.

Each articulated arm 2 comprises a first arm 3, so-called extension arm, allowing a rotational movement of the articulated arm 2 in the direction of the double arrow F1 in a first plane, here substantially parallel to the ceiling of the operating room, i.e. a horizontal plane. The first arm 3 is connected by means of a pivot joint to a second arm, so-called compensation arm or supporting arm 4, allowing a rotational movement of the articulated arm 2 around a pivot axis 8 in the direction of the double arrow F2 in a second plane substantially perpendicular to the first plane, i.e. here a vertical plane.

It will be understood that, while remaining within the scope of the invention, the supporting arm 4 according to the invention could be mounted on a pivot in any other way, for example on another type of suspending device or directly on a wall or a ceiling of a room.

The free end of the supporting arm 4 is intended to support, via a connecting piece 6, a load (not represented) which can be for example an equipment, such as a lighting device, a monitor, a camera, etc, or a medical device, such as a transfusion or perfusion bottle, etc.

Figure 2:
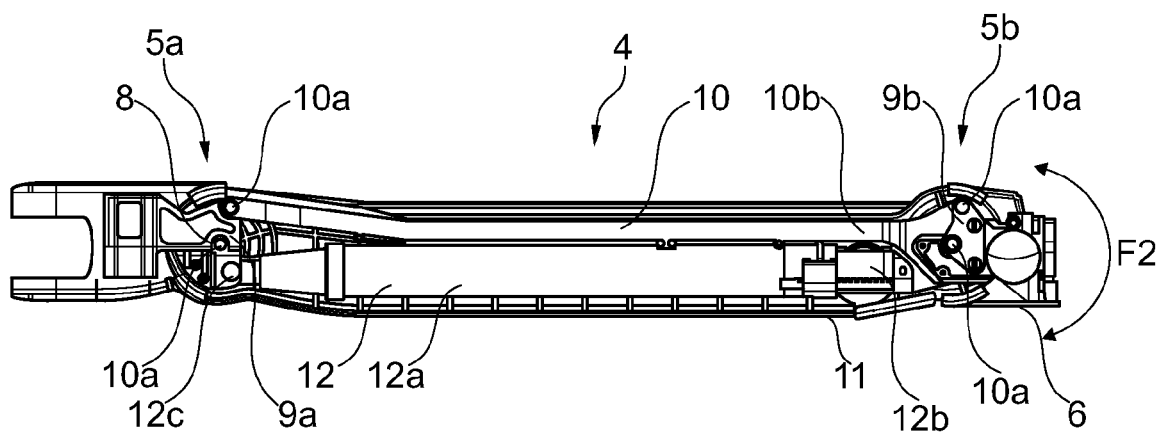
FIG. 2 is a longitudinal view of the supporting arm in FIG. 1, uncovered at the front end, in a first position.

As it can be seen in FIG. 2, the supporting arm 4 comprises a shell 11 whose ends 5a, 5b define the ends of the supporting arm 4. Jacketed in this shell 11, the supporting arm 4 also comprises a fixed link 9a firmly connected to an end 5a of the shell 11 and a mobile link 9b pivotally mounted at the so-called free end 5b of the shell 11. The fixed link 9a and the mobile link 9b are connected to one another by means of a connecting rod 10 mounted so as to pivot at its two ends with respect to the fixed and mobile links 9a 9b. Thus, the shell 11, the connecting rod 10, the fixed link 9a and the mobile link 9b form on the whole a deformable four-pointed parallelogram.

As it can be seen in FIG. 2, the supporting arm 4 also comprises a jack 12, for example a pneumatic jack, connecting the fixed link 9a to the connecting rod 10 and the shell 11. According to another embodiment, the jack can be connected to only one of the rod and the shell or to the mobile link. The jack 12 thus enables to actuate the deformable parallelogram in order to adjust the angular position or slope of the supporting arm 4 with respect to the fixed link 9a while making the supporting arm 4 pivot around the pivot axis 8 in the direction of the double-arrow F2. The deformable parallelogram and the jack 12 thus allow the user to modify in an easy and stable way the position of the supporting arm 4 in order to manually position the load at a desired height.

In a known way per se, the jack 12 is made up of a body 12a in which a piston 12b slides. The body 12a is mounted at its free end so as to swivel on the fixed link 9a in the direction of an axis 12c shifted with respect to the pivot axis 8, and the free end of the piston 12b is connected to the connecting rod 10 and the shell 11 as described below.

Figure 5:
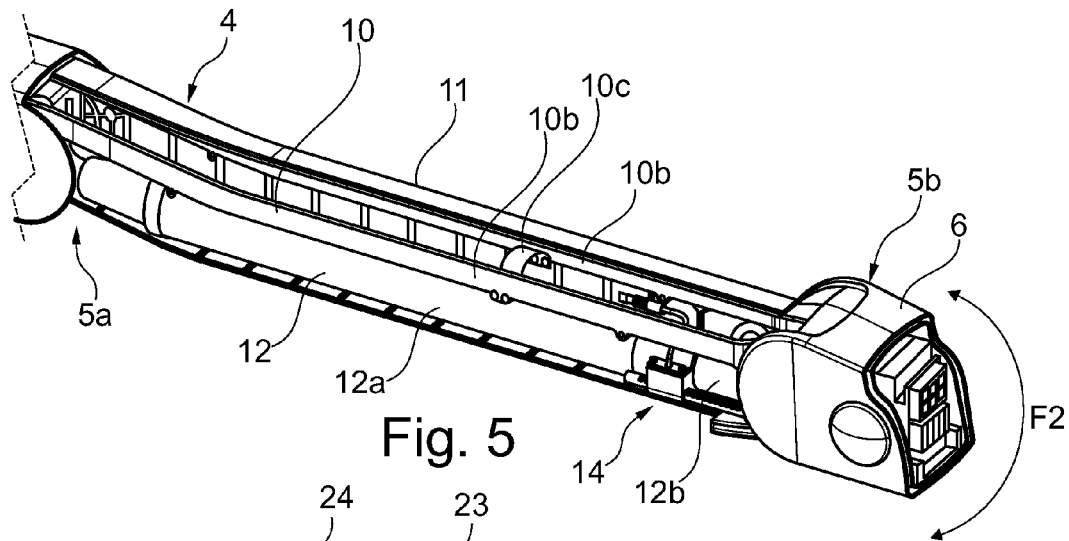
FIG. 5 is a perspective view of the supporting arm in FIG. 2 in the first position thereof.

Advantageously, the connecting rod 10 comprises here two substantially identical bars 10b, parallel to one another so as to jacket the jack 12, and able to be connected together by means of one or more cross-pieces 10c, as it can be better seen in FIG. 5. The connecting rod 10 has here the shape of a Y, the basis of the Y being mounted on the fixed link 9a so as to pivot about a pivot point 10a of the shell 11 shifted with respect to the pivot joint 8 of the supporting arm 4. The free end of one branch of the Y is mounted on the mobile link 9b so as to pivot with respect to a pivot point 10a, the mobile link 9b itself being able to pivot with respect to another pivot point 10a provided at the free end 5b of the supporting arm 4. The free end of the other branch of the Y is connected to the free end of the piston 12b of the jack 12.

Advantageously, the jack 12 is an adjustable-pressure pneumatic jack so that the pressure inside the jack 12 can be adjusted according to the weight of the load supported by the supporting arm 4, as it will be described more in detail below. The gas in the jack 12 can be for example air or nitrogen. The maximum pressure inside the jack 12 is advantageously selected according to the weight of the heaviest load that can be put on the supporting arm 4. For example, when the pressure inside the jack is adjusted between 12 to 30 bars, the supporting arm 4 can support a load up to 40 kg. Preferably, the jack 12 is arranged so as to have a wide range of weights between 5 kg and 40 kg.

Figures 3, 4:
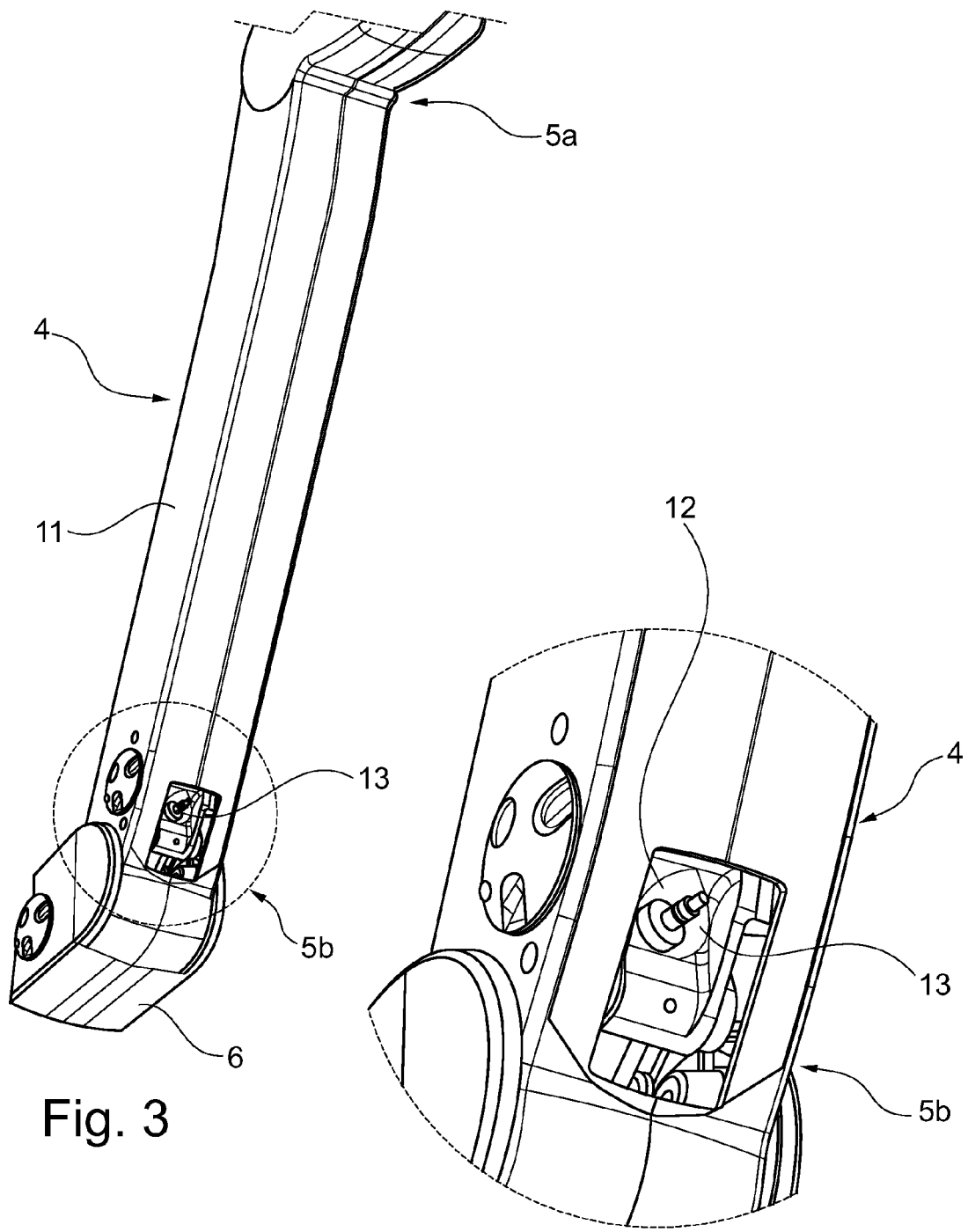
FIG. 3 is a back perspective view of the supporting arm in FIG. 2.
FIG. 4 is a magnified perspective view of a detail of the supporting arm in FIG. 3.

As it can be seen in FIGS. 3 and 4, the supporting arm 4 comprises a valve 13 arranged here directly on the jack 12 in order to connect this jack to a device for adjusting the pressure (not represented) such as a compressor or a pressure tank for example a air or nitrogen pressure tank. The device for adjusting the pressure can be connected to the valve 13 by means of an inflation adaptor to be inserted (not represented). For disconnecting the device for adjusting the pressure, a button (not represented) will be advantageously provided, adjacent to the valve 13, which allows to remove the adaptor from the valve 13. While remaining within the scope of the invention, the valve 13 could be arranged on the shell 11, preferably on a back face of the shell 11, and connected to the jack 12 by means of a flexible adaptor. It will be understood that for ergonomic reasons the valve 13 is preferably arranged along the supporting arm 4 near the free end 5 of the supporting arm 4 so as to be as low as possible and to be more easily reached by the user in order that the user can easily carry out an adjustment of the pressure within the jack 12.

As it can be seen in FIG. 5, the supporting arm 4 moreover comprises a blocking device 14 enabling to block the supporting arm 4 in a plurality angular blocking positions, or slopes, of the supporting arm 4 in the direction of the double-arrow F2. The blocking device 14 is preferably of the mechanical type, and can be made up for example of two complementary mechanical pieces, for example respectively provided with teeth or cogs cooperating with notches, respectively fixed to the body 12a and the piston 12b of the jack 12. In the example represented in FIG. 6, the blocking device 14 comprises a toothed rack 15 fixed to the free end of the piston 12b and cooperating with a latch 16 integral with the body 12a of the jack 12 and mobile along the toothed rack 15. The latch 16 comprises here a sleeve 22 surrounding more precisely the body 12a of the jack 12 in order to firmly connect the latch 16 and the jack 12 together.

Figure 7:
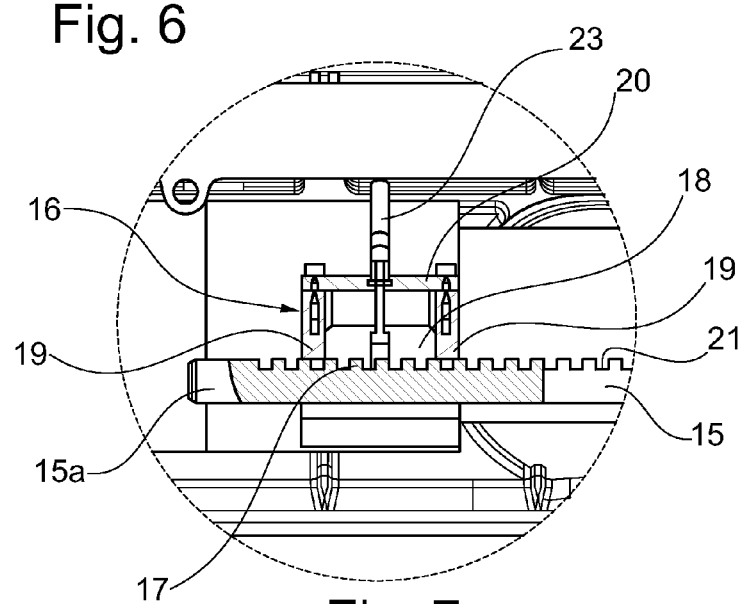
FIG. 7 is a view, along the cutting line VII-VII, of the supporting arm in FIG. 6.

More particularly, as it can be better seen in FIG. 7, the latch 16 comprises at least one cog 17, here a plurality of cogs 17, intended to be inserted into notches 21 in the toothed rack 15 in order to block the supporting arm 4 in a selected angular blocking position. It will be understood that the cogs 17 and the notches 21 are configured so as to have the same pitch and the same module. In the example represented in FIG. 7, the cogs 17 of the latch 16 are formed on an element 18 mobile between two struts 19 of a bracket 20 so as to be able to take a low position (represented in FIG. 7) in which the cogs 17 are inserted into the notches 21 in the toothed rack 15 in order to block any movement of the body 12a of the jack 12 with respect to the piston 12b of the jack 12 and thus to block the supporting arm 4 in the angular position thereof, and a high position of the latch 16 (not represented) in which the cogs 17 are removed from the notches 21 in the toothed rack 15 in order to allow the body 12a of the jack 12 to move with respect to the piston 12b of the jack 12 and thus the supporting arm 4 to move angularly in the direction of the double-arrow F2 represented for example in FIG. 5.

In addition, the mobile element 18 of the latch 16 is connected to a flexible connector 23 running along the jack 12 and having at its free end opposite the element 18 a serrated roller 24 allowing a user to make the element 18 slide between the struts 19. The serrated roller 24 moreover allows the user to easily block the element 18 at a high or low position on the toothed rack 15.

Figure 6:
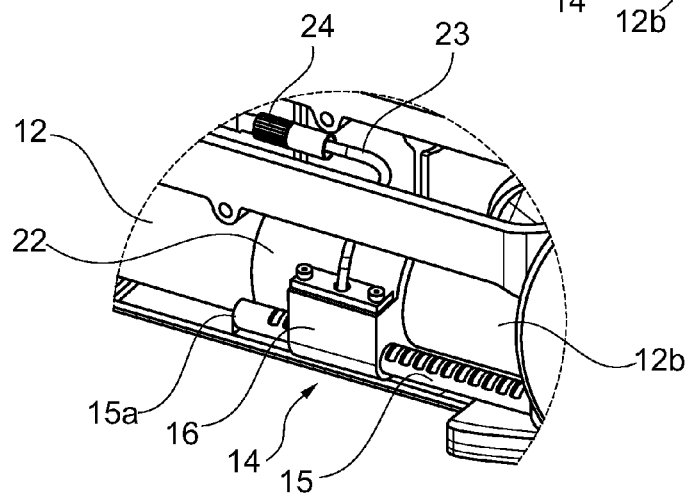
FIG. 6 is a magnified perspective view of a detail of the supporting arm in FIG. 5.
Figure 9:
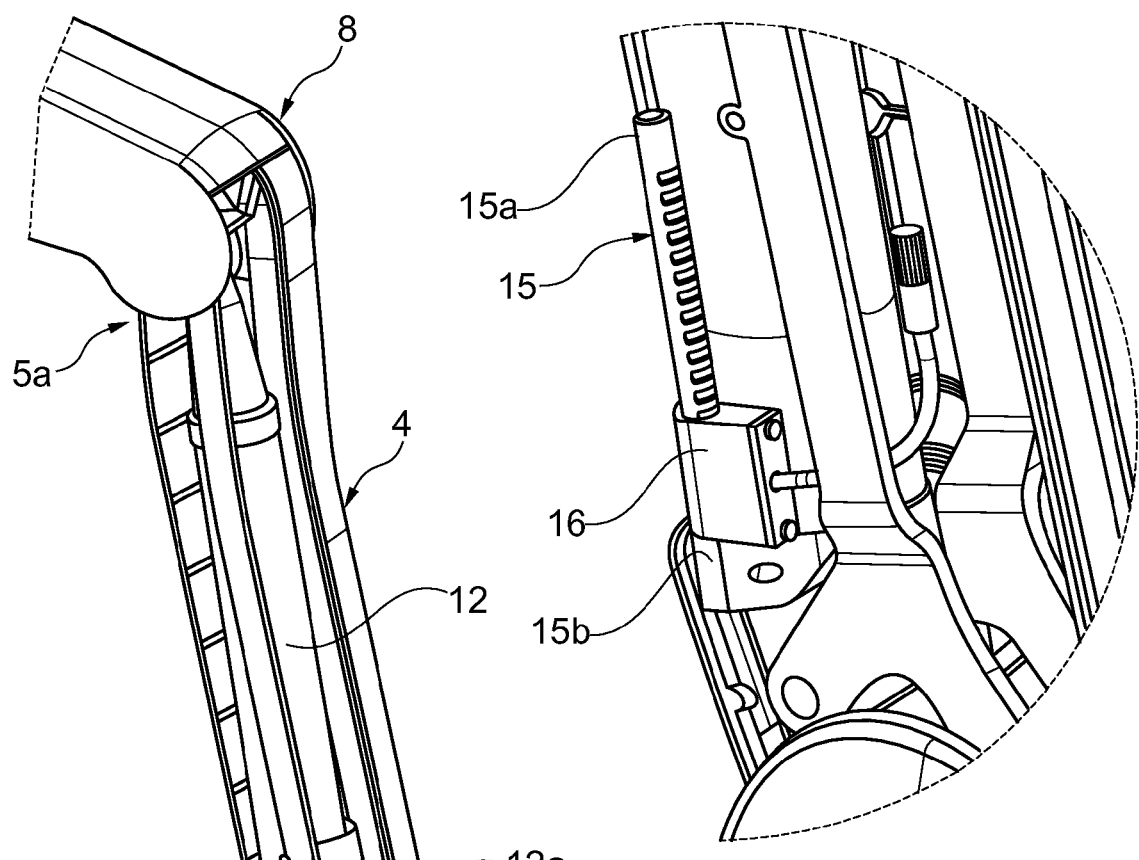
FIG. 9 is a magnified perspective view of a detail of the supporting arm in FIG. 8.
Figure 8:
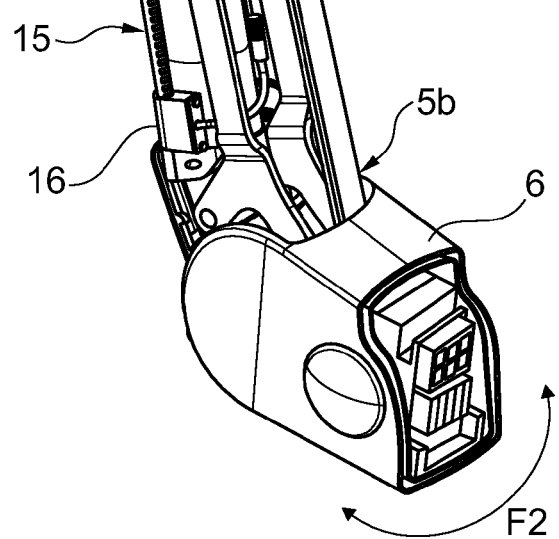
FIG. 8 is a perspective view of the supporting arm in FIG. 2 in a second position.

As an example, in FIG. 5, the supporting arm 4 is represented in a first position, slightly lowered and close to the horizontal position, which corresponds to a position of the latch 15 close to the free end 15a of the toothed rack 15 as it can be better seen in FIGS. 6 and 7. In FIGS. 8 and 9, the supporting arm 4 is represented in a second position, very lowered and close to the vertical position, corresponding to a position of the latch 15 against the end 15b of the toothed rack 15 opposite the free end 15a.

Figure 10:
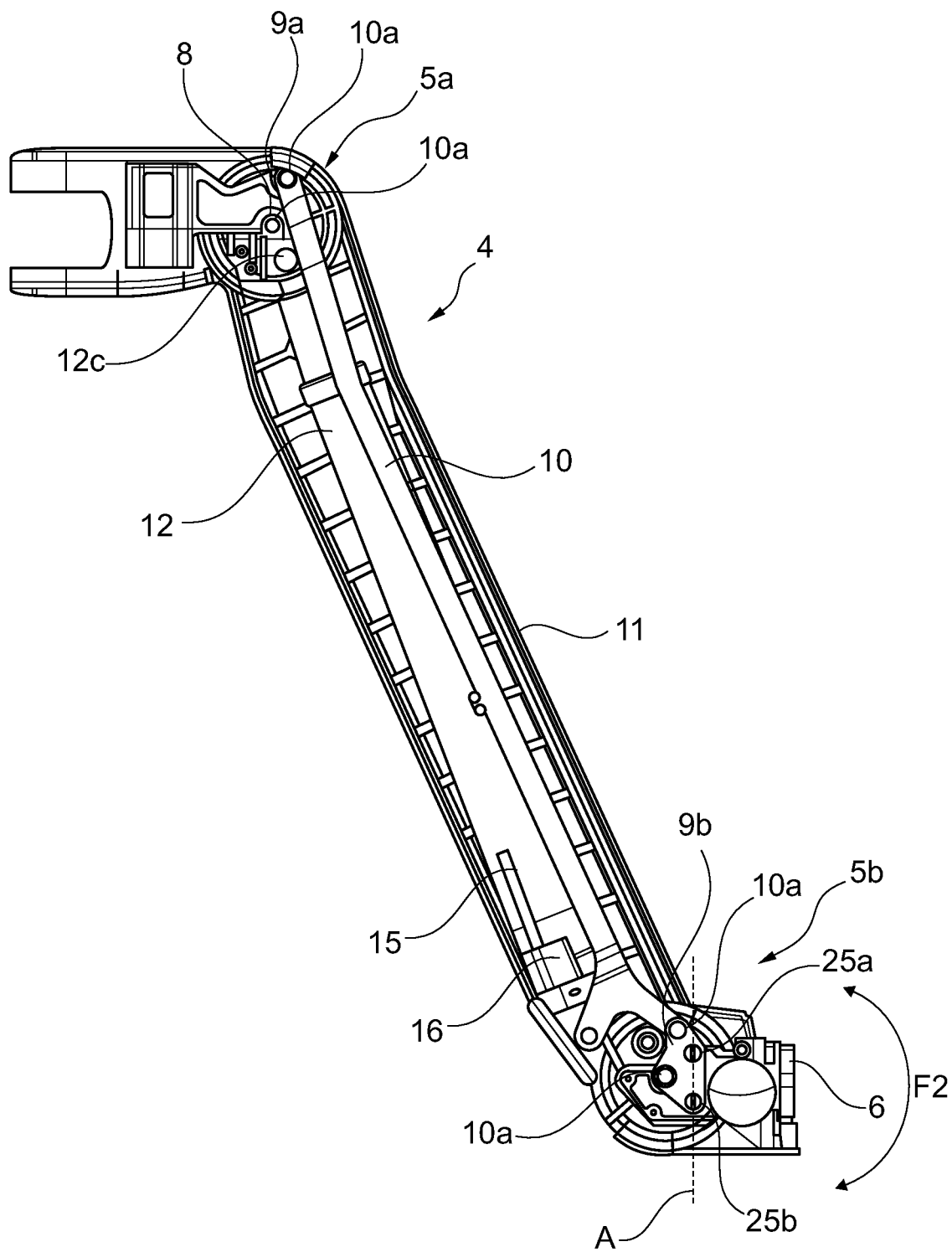
FIG. 10 is a longitudinal view of the supporting arm in FIG. 2, uncovered at the front end, in the second position thereof.
Figure 11:
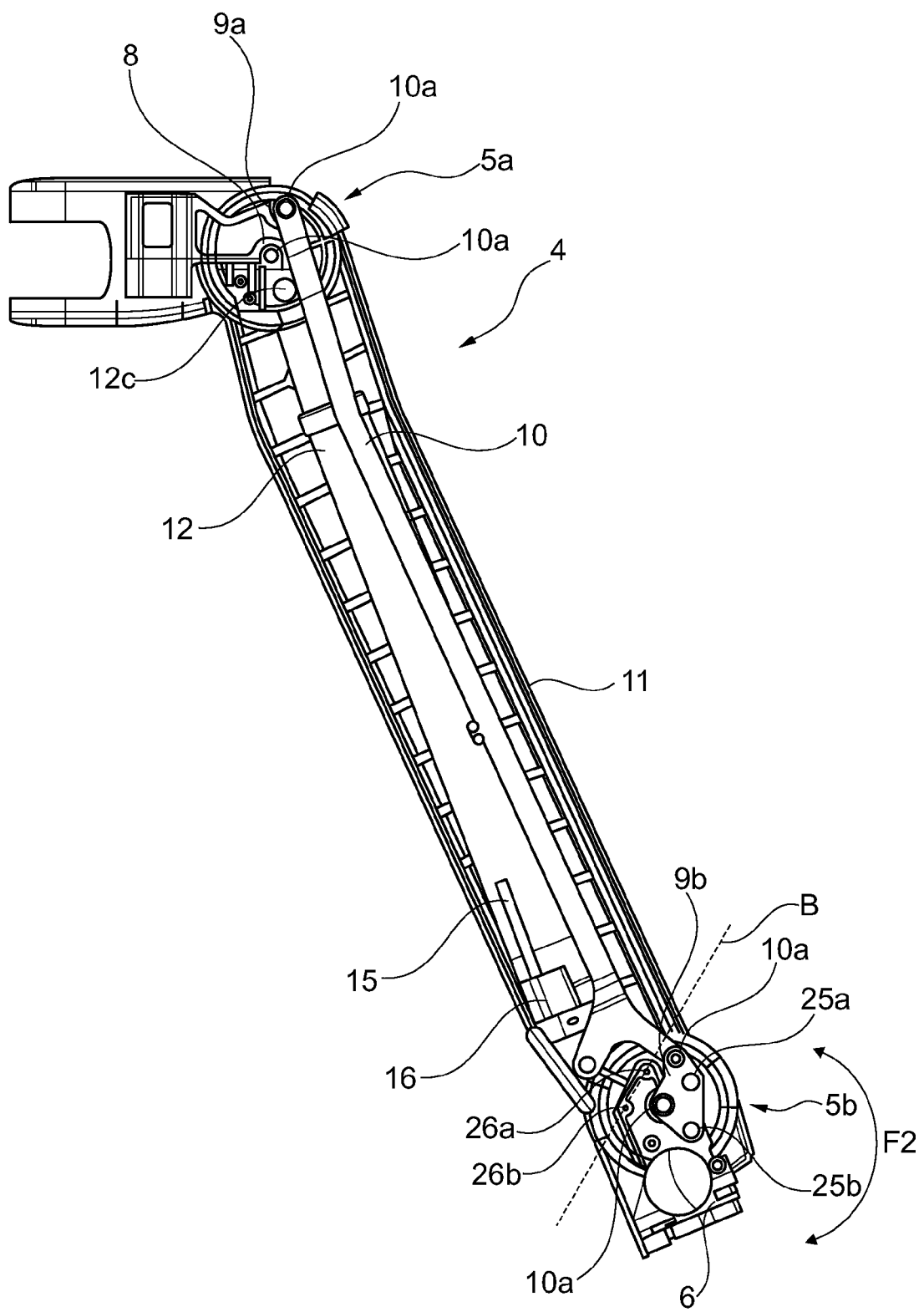
FIG. 11 is a longitudinal view, similar to FIG. 10, of the supporting arm in another position.

FIGS. 10 and 11 show the supporting arm 4 without any front cover for better showing how the connecting piece 6 is fixed to the free end 5 of the supporting arm 4 according to two configurations of the supporting arm 4.

More precisely, in a first configuration of the supporting arm 4 represented in FIG. 10, the supporting arm 4 is arranged so that the connecting piece 6 arranged at the free end 5 of the supporting arm 4 keeps its orientation with respect to the fixed link 9a when the supporting arm 4 pivots around the pivot axis 8 in the direction of the double arrow F2. In the example represented in FIG. 10, the connecting piece 6 is fixed on the mobile link 9b at a first couple of points 25a, 25b, here by means of two screws. In this manner, the connecting piece 6 has an axis of orientation A that is fixed with respect to the fixed link 9a, which remains parallel to the fixed link 9a of the parallelogram when the supporting arm 4 pivots around the pivot axis 8 in the direction of the arrow F2 and changes slope. It is thus understood that, in the configuration represented in FIG. 10, the axis A of the connecting piece 6 remains vertical when the supporting arm 4 changes slope.

In an alternative embodiment, in a second configuration of the supporting arm 4 represented in FIG. 11, the supporting arm 4 is arranged so that the connecting piece 6 is oriented so as to follow the slope of the supporting arm 4 when the supporting arm 4 pivots around the pivot axis 8 in the direction the double arrow F2. Thus, the orientation of the connecting piece 6 is fixed with respect to the connecting rod 10 but variable with respect to the fixed link 9a. In FIG. 11, the connecting piece 6 is fixed on the shell 11 at a second couple of points 26a, 26b, here also by means of two screws. It is understood that, in this configuration, the first couple of points 25a, 25b are not used. In this manner, the connecting piece 6 has an axis B which is integral with the shell 11 of the supporting arm 4 and thus has a variable orientation when the supporting arm 4 pivots around the pivot axis 8 in the direction the arrow F2 and changes slope in the direction of the arrow F2. It is thus understood that, in the configuration represented in FIG. 11, the axis B of the connecting piece 6 does not remain vertical when the arm supporting 4 changes slope.

For putting a load onto a supporting arm 4 according to the invention, the user starts with blocking the supporting arm 4 in a desired blocking position, having an unspecified slope, by inserting the cogs 17 of the latch 16 into the notches 21 in the toothed rack 15 provided to this end. To do this, the user can advantageously turn the serrated roller 24 of the flexible connector 23 associated with the cogs 17. Then, if necessary, the user can remove the load already on the supporting arm 4.

The user then puts a load onto the connecting piece 6.

According to the weight of the load thereon, the user advantageously adjusts the pressure inside the jack 12 via the valve 13 by connecting a device for adjusting the pressure in a known way per se. The maximum pressure inside the jack 12 is preferably selected according to the maximum admissible load weight to be fixed at the end 5 of the supporting arm 4. As an example, the pressure can be adjusted at 30 bars if the maximum admissible load weight is 40 kilograms. The user can thus pass very easily from one load to another, heavier or lighter.

Once the pressure inside the jack 12 is adjusted, the user can unblock the supporting arm 4, by removing the cogs 17 of the latch 16 from the notches 21 in the toothed rack 15, by turning the serrated roller 24 of the flexible connector 23. Thanks to the retaining force exerted by the jack 12, the supporting arm 4 then remains in position. The supporting arm 4 is then ready to be moved in all the slope positions desired by the user by making it pivot around the pivot axis 8 in the direction of the arrow F2 represented for example in FIG. 1.

In particular, once the pressure inside the jack 12 is adjusted to the maximum weighting load supported by the supporting arm 4, one can advantageously put onto the supporting arm 4 a variable weighting load, as for example a perfusion pocket intended to empty in time or any other medical device of variable weight.

Of course, the present invention is not limited to the preceding description of embodiments which can be somewhat modified while remaining within the scope of the invention.

The invention claimed is:

1. An adjustable-position load supporting arm comprising a framework having on the whole the shape of a deformable parallelogram provided with at least a fixed link, a mobile link, a first and a second mobile connecting rod and a free end able to support a load, a jack comprising a body and a piston one of which is coupled with the fixed link, the other of which is coupled with at least one of the first and second connecting rods, said jack being able to actuate said first and second connecting rods with respect to said fixed link so as to deform said deformable parallelogram, said jack being of the adjustable-pressure type so that the pressure inside said jack is adjustable according to the weight of said load supported by said supporting arm, wherein said mobile link is mounted to said supporting arm only at said free end whereas said fixed link is mounted to said supporting arm only at an end of said supporting arm opposite said free end of said supporting arm formed by said first and second mobile connecting rods and wherein said supporting arm further comprises, at said free end, a connecting piece able to support said load and to be firmly connected to:
   in a first configuration, said mobile link so as to have an axis of orientation (A) that is fixed with respect to said fixed link and variable with respect to said first and second connecting rods when said supporting arm shifts position,
   in a second configuration, at least one of said first and second connecting rods so as to have an axis of orientation (B) that is variable with respect to said fixed link and fixed with respect to said first and second connecting rods when said supporting arm shifts position.

2. A supporting arm according to claim 1, moreover comprising a device for blocking the angular position of said first, second connecting rod with respect to said fixed link, said blocking device comprising a toothed rack and a latch one of which is firmly connected to the body of the jack, the other of which is firmly connected to the piston of the jack, said latch being arranged so as to be mobile along said toothed rack and able to cooperate with said toothed rack so as to block the angular position of said first, second connecting rod with respect to said fixed link in a plurality of blocking positions.

3. A supporting arm according to claim 2, in which said latch comprises at least one cog intended to be inserted into a notch in said toothed rack in order to block said supporting arm in position.

4. A supporting arm according to claim 1, moreover comprising a valve coupled with said jack and intended to connect said jack to a device for adjusting the pressure in the jack.

5. A supporting arm according to claim 1, comprising at least one shell forming said second connecting rod jacketing said first connecting rod.

6. A supporting arm according to claim 1, in which said first connecting rod has the shape of a Y whose basis is swivelingly mounted on said fixed link, one branch of which has a free end swivelingly mounted on said mobile link and the other branch of which has its free end connected to one end of said jack, the other end of said jack being able to swivel with respect to said fixed link.

7. A load suspending device comprising:
   at least one articulated arm having a first arm arranged so as to be rotatingly mobile according to a rotational movement (F1) in a first plane, and
   a load supporting arm comprising a framework having on the whole the shape of a deformable parallelogram provided with at least a fixed link, a mobile link, a first and a second mobile connecting rod and a free end able to support a load, a jack comprising a body and a piston one of which is coupled with the fixed link, the other of which is coupled with at least one of the first and second connecting rods, said jack being able to actuate said first and second connecting rods with respect to said fixed link so as to deform said deformable parallelogram, said jack being of the adjustable-pressure type so that the pressure inside said jack is adjustable according to the weight of said load supported by said supporting arm, wherein said mobile link is mounted to said supporting arm only at said free end whereas said fixed link is mounted to said supporting arm only at the an end of said supporting arm opposite said free end of said supporting arm formed by said first and second mobile connecting rods and wherein said supporting arm further comprises, at said free end, a connecting piece able to support said load and to be firmly connected to (i) said mobile link in a first configuration, so as to have an axis of orientation (A) that is fixed with respect to said fixed link and variable with respect to said first and second connecting rods when said supporting arm shifts position, and (ii) at least one of said first and second connecting rods in a second configuration, so as to have an axis of orientation (B) that is variable with respect to said fixed link and fixed with respect to said first and second connecting rods when said supporting arm shifts position,
   said load supporting arm being connected to said first arm by means a pivot joint arranged so as to rotate according to a rotational movement (F2) in a second plane distinct from said first plane.

* * * * *